United States Patent [19]

Gerondale

[11] Patent Number: 5,447,230
[45] Date of Patent: Sep. 5, 1995

[54] PACKAGE FOR SURGICAL INSTRUMENTS

[75] Inventor: Scott J. Gerondale, Maineville, Ohio

[73] Assignee: Ethicon, Inc., Somerville, N.J.

[21] Appl. No.: 333,081

[22] Filed: Oct. 2, 1994

Related U.S. Application Data

[63] Continuation of Ser. No. 96,091, Jul. 23, 1993, abandoned.

[51] Int. Cl.6 ............... B65D 83/10; B65D 73/00; A61B 17/06
[52] U.S. Cl. .................... 206/363; 206/364; 206/438; 206/467; 206/470; 229/167
[58] Field of Search ............ 206/216, 363, 364, 370, 206/461, 570, 438, 467, 469, 470, 439; 229/167, 120.18, 120.21

[56] References Cited

U.S. PATENT DOCUMENTS

| | | | |
|---|---|---|---|
| 2,308,818 | 1/1943 | Levkoff | 229/167 |
| 3,324,999 | 6/1967 | Farquhar | 229/167 |
| 3,368,735 | 2/1968 | Levi | 229/167 |
| 4,423,732 | 1/1984 | Tarjan et al. | 206/438 |
| 4,697,703 | 10/1987 | Will | 206/363 |
| 4,736,850 | 4/1988 | Bowman et al. | 206/438 |
| 5,029,709 | 7/1991 | Faulstick | 229/167 |
| 5,082,112 | 1/1992 | Dunklee | 206/363 |

Primary Examiner—Steven N. Meyers
Assistant Examiner—Marie Denise Patterson
Attorney, Agent, or Firm—Paul A. Coletti

[57] ABSTRACT

An outer package for a thermoformed blister package, wherein the blister package has an outwardly extending flange. The outer package has foldably connected inner flange support members to support the outwardly extending flange of the blister package and stiffen the package.

6 Claims, 5 Drawing Sheets

PACKAGE FOR SURGICAL INSTRUMENTS

This is a continuation of application Ser. No. 08/096,091, filed Jul. 23, 1993, now abandoned.

TECHNICAL FIELD

The field of art to which this invention relates is packaging, in particular, packages for surgical instruments.

BACKGROUND OF THE INVENTION

Endoscopic surgical instruments have been developed for use in endoscopic surgical procedures. The endoscopic surgical instruments, although rugged, must be properly packaged for sterilization and shipment and handling in order to prevent damage to the instruments. Many endoscopic surgical instruments are packaged in conventional thermoformed plastic blister packages. Thermoformed blister packages are well known and are manufactured using conventional thermoforming processes wherein a sheet of polymer is typically heated and drawn by a vacuum into a mold. The thermoformed blister packages are typically designed to have a number of cavities which conform to the contours of particular surgical instruments. The surgical instruments are placed within these cavities and the cavities serve to both retain and cushion the instruments during sterilization, shipping and handling. Many thermoformed blister packages consist of a relatively rigid, thermoformed polymer lower tray and a flexible polymer cover which is typically gas permeable. The cover may also be a thermoformed polymer cover and may have cavities. A flange typically extends about the outer periphery of the blister tray to which the cover is sealed. The sealing may be accomplished by a number of conventional processes including ultrasonic welding, heat sealing and the use of various adhesives and bonding agents.

For shipment, handling and storage, it is necessary to place the blister packaged instrument into an outer package. The outer package serves several functions. It protects the blister package from inadvertent cuts, punctures and tears thereby preventing the compromising of the sterility of the instrument. The package also serves to add a degree of additional protection to the blister package in the event of accidental drops or impacts.

It is especially critical in packaging a sealed, blister packaged, sterile instrument to protect the seal of the blister package. Although most thermoformed blister trays are relatively rigid, they are still capable of flexing during normal shipping, handling and storage. This flexing is known to cause the flanges to twist and bend. Such movements can potentially cause the cover seal to delaminate in those areas where the twisting or torsional forces and/or bending are extreme or where the seal may be weak. Delamination will typically result in the compromise of the sterility of the interior of the package and its contents. This can be a major problem since most disposable medical instruments and medical devices cannot be re-sterilized in the field. In order to prevent this type of flexing, it is necessary to somehow support the flanges of the blister package when it is inserted into an outer package and to stiffen the outer package. Present approaches utilize massive amounts of polymeric foams, such as polyurethane foam, to cushion and protect the packages and support the flanges. There are various disadvantages associated with polymeric foam. One disadvantage is that in order for the foam to be effective, a relatively large quantity of the foam is required thereby increasing the size of an outer box into which the blister packed instrument is packaged. Another disadvantage of the polymeric foams is the fact that they are difficult to dispose of and recycle. Yet another disadvantage is that larger outer boxes are required for a foam packed blister package resulting in additional shelf space in a hospital supply storage area being taken up.

Therefore, it is an object of the present invention to provide an outer package for a thermoformed blister packaged endoscopic instrument which supports the flanges of the blister packages without the need for a polymeric foam outer cushion.

It is a further object of the present invention to provide a package which supports the flange of a blister package thereby minimizing twisting and flexing and bending of the flange of the blister package and decreasing the possibility of a seal delaminating.

It is yet a further object of the present invention to provide a package for a blister package which has improved stiffness.

SUMMARY OF THE INVENTION

Accordingly, an outer package for a thermoformed, blister package having an outwardly extending flange is disclosed. The outer package is a foldable package which has a base panel having a pair of opposed major sides and a pair of opposed minor sides. A first side panel having a pair of opposed major sides and a pair of opposed minor sides is foldably connected along a first major side to one major side of the base panel. A closure flap is foldably connected to the other major side of the base panel. A top panel having a pair of opposed major sides and a pair of opposed minor sides is foldably connected along its first major side to the second major side of the top panel. A first top support panel have a pair of opposed major sides and a pair of opposed minor sides is foldably connected along a first major side to the second major side of the second side panel. A first side support panel having a pair of opposed major sides and a pair of opposed minor sides is foldably connected along a first major side to the second major side of the first top support panel. A connecting panel having a pair of opposed major sides and a pair of opposed minor sides is foldably connected along a first major side to the second major side of the first side support panel. A second side support panel having a pair of opposed major sides and a pair of opposed minor sides is foldably connected along its first major side to the second major side of the connecting panel. A second top support panel having a pair of opposed major sides and a pair of opposed minor sides is foldably connected along a major side to the second major side of the second side support panel. A closure means is foldably connected to each minor end of the base panel. In a preferred embodiment the closure means comprises an outer flap panel having a pair of opposed minor sides and a pair of opposed major sides foldably connected to a minor side of the base panel. A bottom flap panel having a pair of opposed major sides and a pair of opposed minor sides is foldably connected along a first major side to the second major side of the outer flap panel. An inner flap panel having a pair of opposed major sides and a pair of opposed minor sides is foldably connected along a first major side to the second major side of the bottom flap panel. A top flap panel having a pair of opposed major sides and a pair of opposed minor sides is foldably connected along a first major side to the second major side of the inner flap panel. The package optionally comprises locking tabs and tab pockets for locking the end flaps.

Another aspect of the present invention is the combination of a thermoformed, sealed blister package and the above-described foldable outer package.

Other features and advantages of the invention will become more apparent from the following description and accompanying drawings.

BEST MODE FOR CARRYING OUT THE INVENTION

The package 10 of the present invention is illustrated in FIGS. 1-7.

Figure 3:
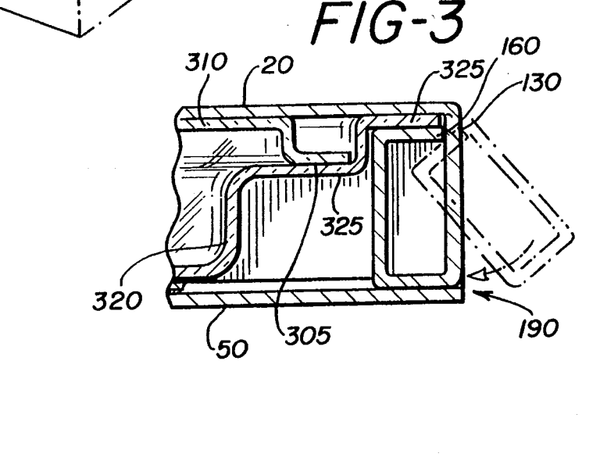
FIG. 3 is a partial cutaway view taken along View Line 3—3 of FIG. 1 illustrating the end flap of the package of the present invention supporting an end flange of the thermoformed blister package.
Figure 4:
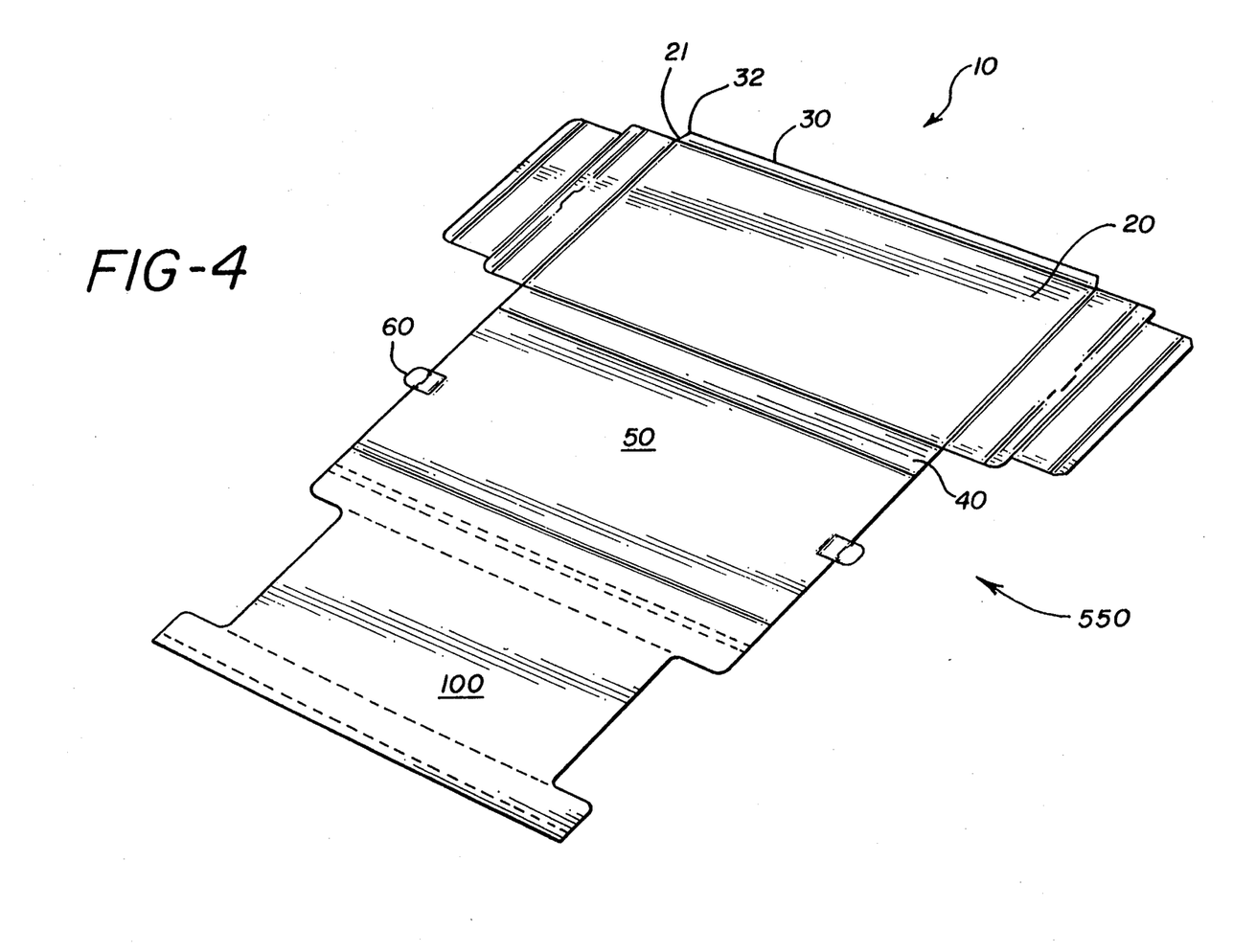
FIG. 4 is a perspective view of the outer package of the present invention prior to folding and assembly.
Figure 4A:
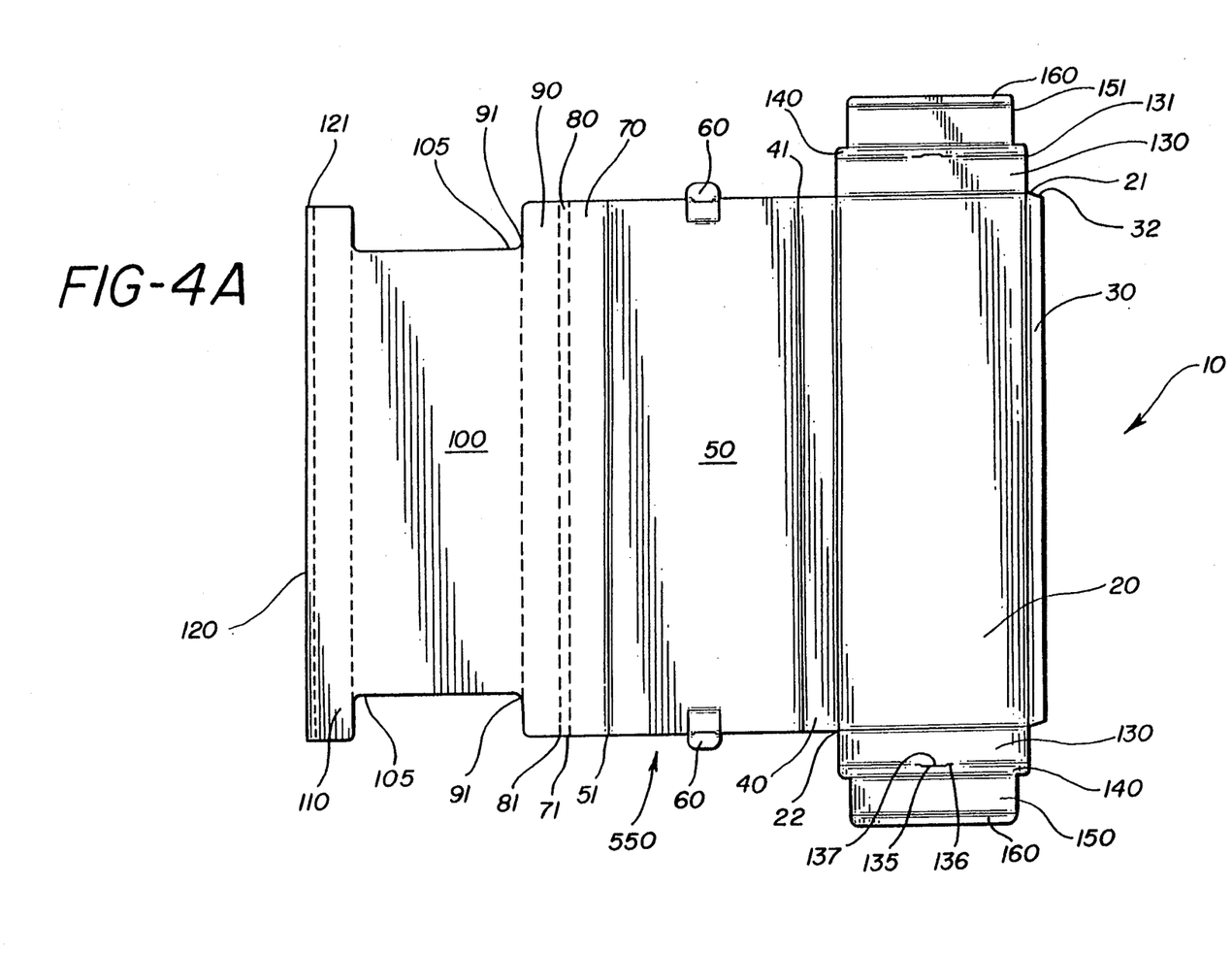
FIG. 4A is a plan view of the outer package of the present invention prior to folding assembly.

Referring to FIGS. 4 and 4A, the outer foldable package 10 of the present invention is seen prior to folding and assembly. The package 10 is seen after assembly in FIGS. 1-3. The outer package 10 is seen to have base panel 20. The base panel 20 is seen to be substantially rectangular having a pair of opposed major sides and a pair of opposed minor sides. Foldably connected to one major side of the base panel 20 along fold line 21 is the closure flap 30. The closure flap 30 is seen to be a substantially rectangular panel having angulated minor ends 32. Foldably connected to the other major side of base panel 20 along fold line 22 is the first side panel 40. The first side panel 40 is seen to be a substantially rectangular panel having a pair of opposed major sides and a pair of opposed minor sides. Foldably connected to the first side panel 40 along fold line 41 is the top panel 50. Top panel 50 is a substantially rectangular panel having a pair of opposed major sides and a pair of opposed minor sides. Extending from the center of both minor sides of top panel 50 are the closure tabs 60.

Foldably connected to the other major side of the top panel 50 along fold line 51 is the second side panel 70. The second side panel 70 is seen to be a substantially rectangular panel having a pair of opposed major sides and pair of opposed minor sides. Foldably connected to the second side panel 70 is the first top support panel 80. First top support panel 80 is foldably connected to second side panel 70 along fold line 71. First top support 80 is seen to have a substantially rectangular configuration and to have a pair of substantially opposed major sides and a pair of substantially opposed minor sides. Foldably connected to first top support panel 80 along fold line 81 is the first side support panel 90. First side support panel 90 is seen to be substantially rectangular with a pair of opposed major sides and a pair of opposed minor sides. Foldably connected to the first side support panel 90 along fold line 91 is the connecting panel 100. Connecting panel 100 is seen to have a shorter length than first side support panel 90. The connecting panel 100 is seen to have a rectangular shape with a pair of opposed major sides and a pair of opposed minor sides. The connecting panel 100 is seen to have rounded corners 105. The second side support panel 110 is foldably connected to the connecting panel 100 along fold line 101. The second side support panel 110 is seen to be longer than the connecting panel 100. The second side support panel 110 is seen to be substantially rectangular in shape with a pair of opposed minor sides and a pair of opposed major sides. As mentioned previously, the corners 105 of connecting panel 100 adjacent to the intersection with first side panel support panel 90 and second side support panel 110 are seen to be rounded. Second top support panel 120 is seen to be substantially rectangular in configuration having a pair of opposed major sides and a pair of opposed minor sides. Second top support panel 120 is seen to foldably connected to second side support panel 110 along fold line 121.

Connected to each minor end of the base panel 20 is an outer flap panel 130. The outer flap panel 130 is seen to have a substantially rectangular configuration. Foldably connected along fold line 131 to each outer flap panel 130 is a bottom flap panel 140. The bottom flap panel 140 is similarly rectangular in configuration. The substantially rectangular inner flap panel 150 is seen to be connected to the bottom flap panel 140 along fold line 141. The inner flap panel 150 is seen to be shorter in length than the outer flap panel 130 and the bottom flap panel 140 and is centered on the bottom flap panel 140 along fold line 141. Foldably attached to each inner flap panel 150 along fold line 151 is the top flap panel 160. The top flap panel 160 is seen to be substantially rectangular in shape. The top flap panel 160 is seen to have rounded corners 162. The slots 135 are seen to be contained in outer flap panels 130 and bottom flap panels 140 along fold line 131. The slit 135 forms a pocket 136 to receive the tab member 60 and also forms tab member 137.

Although the panels of the package 10 have been described as being rectangular in shape and having opposed minor and opposed major sides, it will be appreciated by those skilled in the art that all or some of the panels may have different shapes, e.g., a square shape. In addition, although not preferred, the panels may have one or more curved, rounded or sloping sides.

A sealed, sterile thermoformed blister package 300 is seen in FIGS. 1, 2, 3, and 7 to have lower tray 320 and upper cover 310. The tray 320 has cavities 322 for receiving a surgical instrument 500. Although a circular stapler is seen illustrated in FIG. 1 as instrument 500, it will be appreciated that any surgical instruments or devices or multiple instruments or devices are typically packaged in packages 300. The top or upper cover 310 may have similar cavities 312. Extending from the top of tray 320 is the outwardly extending flange 325. The top cover 310 is sealed to the flange 325 of tray 320 to produce seal 305. The sealing process utilized may be any conventional process used to seal covers to blister trays including ultrasonic welding, adhesives, bonding agents, heat sealing, etc. The surgical instrument is typically contained within the cavities 322 of the tray 320.

Tray 320 and cover 310 are typically made from conventional thermoformed material such as PVC, Polystyrene, and T Polymer (acrylic resin). The blister tray 320 is manufactured using conventional thermoforming equipment and conventional thermoforming processes. The cover 310 may also be made from conventional materials including paper, polymers, and Tyvek ®. As previously mentioned, the top cover 310 is bonded to flange 325 of tray 310 to form seal 305 using conventional methods such as ultrasonic bonding, heat sealing, adhesives and the like. The sealed package 300 containing at least one surgical instrument 500 is sterilized using conventional sterilization processes including sterilant gasses such as ethylene oxide, radiation, autoclaving and the like and equivalents thereof.

The package 10 may be made from any conventional packaging materials, preferably medical grade, including fiber board, paper, plastics, composites and the like having sufficient rigidity to effectively function in a package. The package 10 of the present invention is preferably made of conventional packaging materials such as solid bleached sulphate, clay coated fiberboard or other similar fiberboard materials. The materials will be sufficiently stiff to effectively provide structural rigidity in package 10.

The package 10 will typically be manufactured by conventional methods such as dye cutting, scoring, and gluing. The assembled package 10 will have a sufficient height and sufficient width to effectively support the flange 325 of tray 320 when the package 300 is placed within package 10. The underside of flanges 325 will typically be in contact when in package 10 with first top support panel 80, second top support panel 120, and each top flap panel 160.

Figures 5, 5A:
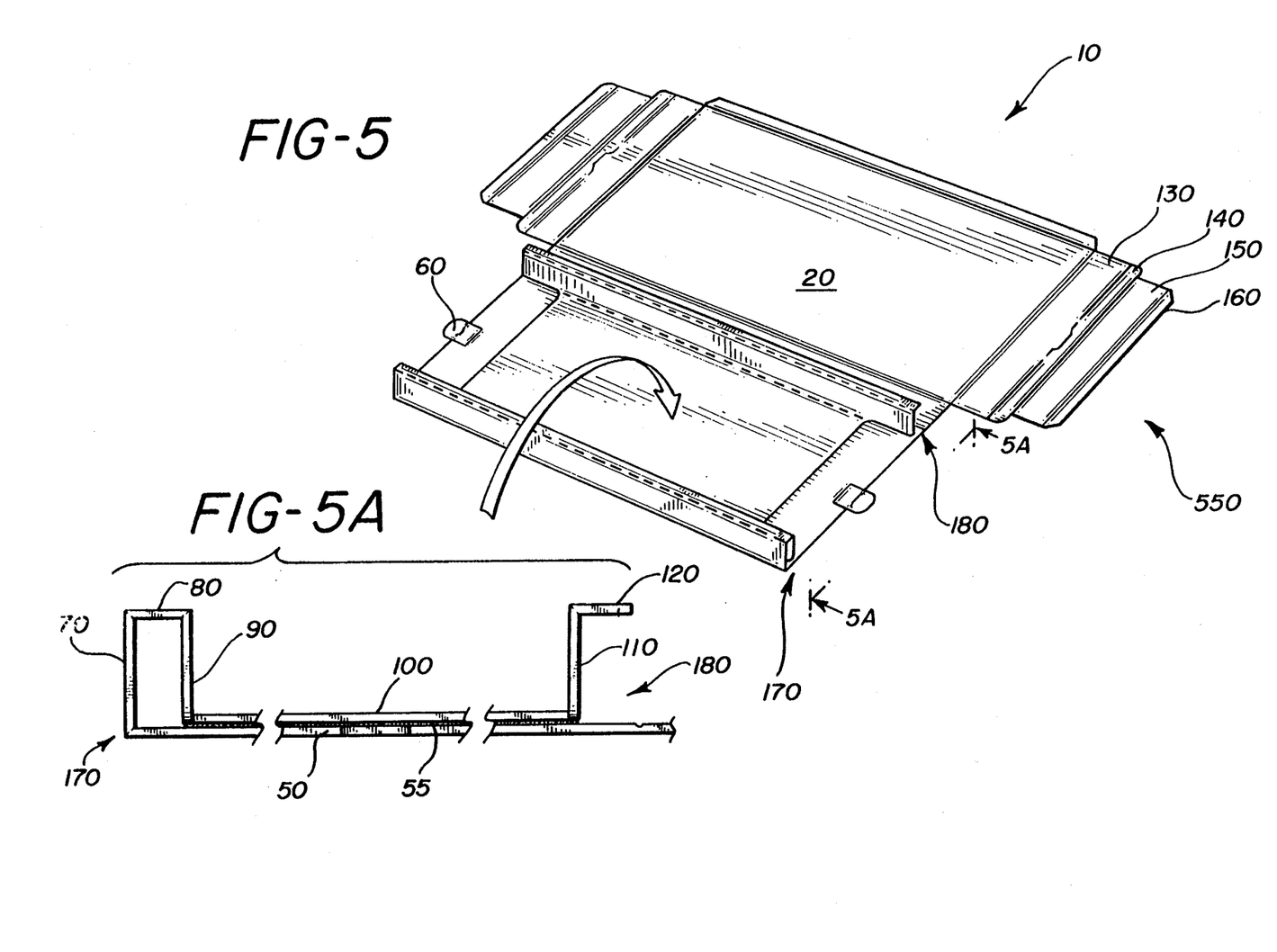
FIG. 5 is a perspective view of package of the present invention, partially, assembled wherein the connecting panel has been mounted onto the base panel and the side flange supports have been formed.
FIG. 5A is an end view taken along View Line 5A—5A of FIG. 5 showing the connecting panel mounted to the base panel.
Figure 6:
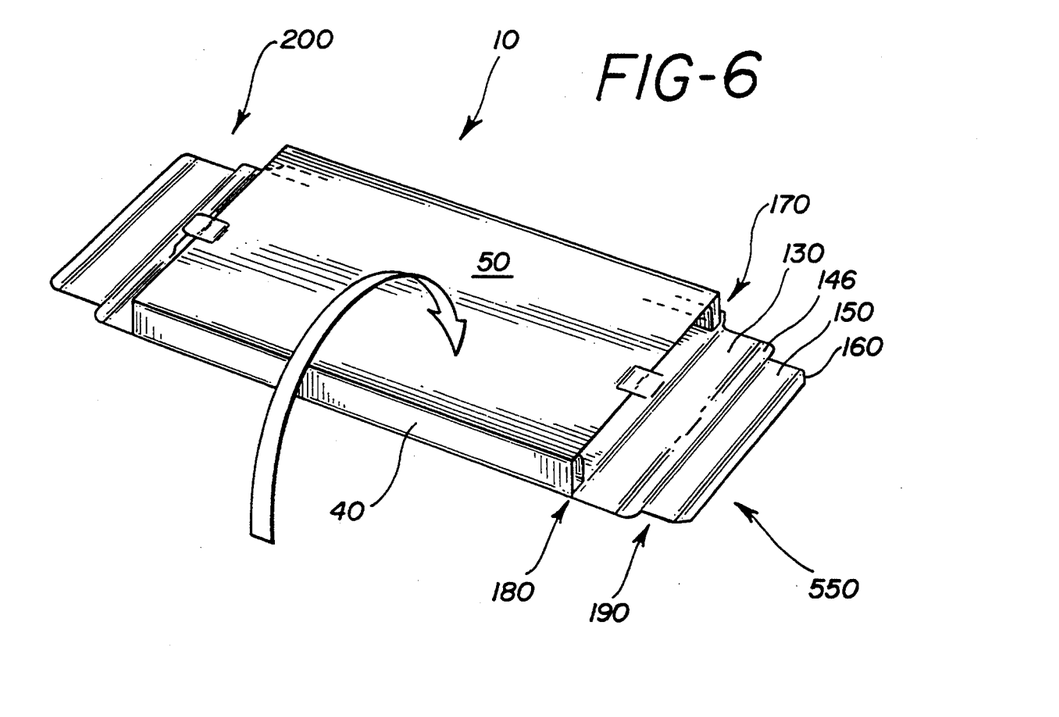
FIG. 6 is a perspective view of the package of the present invention showing the top panel folded over the base panel.
Figure 7:
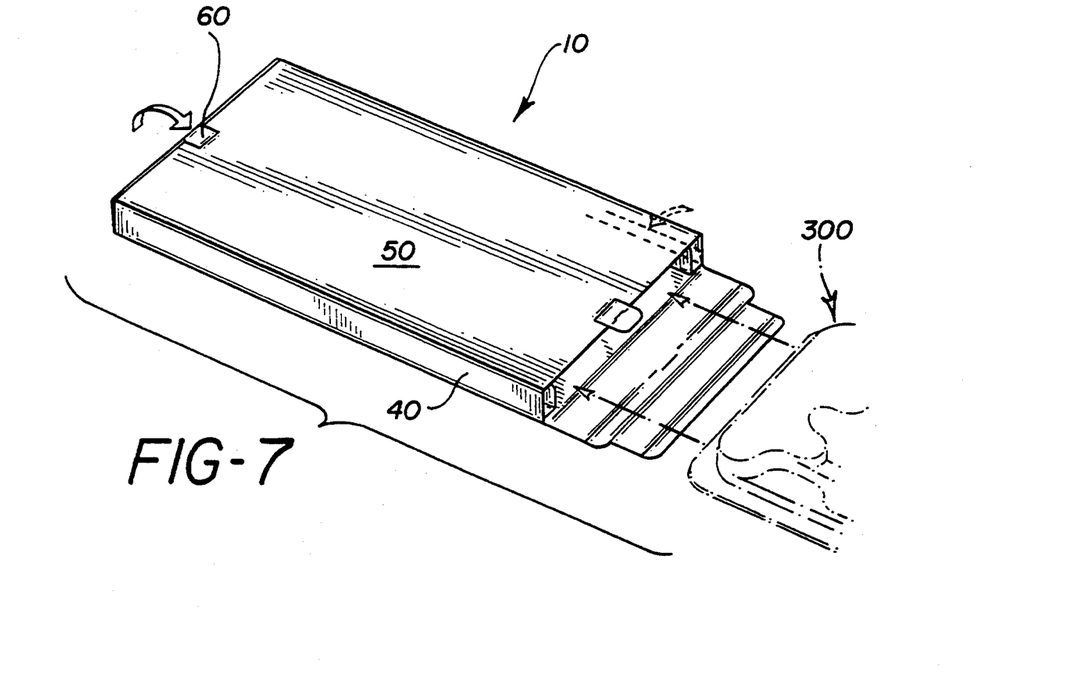
FIG. 7 is a perspective view of the package of the present invention illustrating the insertion of a thermoformed, sealed sterile package containing a surgical instrument into the outer assembled package of the present invention. One end closure flap has been secured in place with a locking tab.

The referring to FIGS. 3, 4, 4A, 5, 5A, 6, and 7 the package 10 of the present invention is seen to be assembled in the following manner. It should be noted that the assembly will consist of a series of folding steps along various fold lines. Depending upon the particular preference of the assembler, the folding sequence steps may be varied. Direction of rotation is made with reference to the end of the package 10 as seen in the direction of arrow 550. Initially, the package 10 is secured so that the base panel 20 and the top panel 50 and the connecting panel 100 are maintained in a stationary position. Then, second top support panel 120 is rotated clockwise about fold line 121 until the second top support panel 120 is perpendicular to second side support panel 110. Next, second side support panel 110 is rotated counter-clockwise about fold line 101 until the second side support panel 110 is perpendicular to connecting panel 100. Then, second side panel 70 is rotated clockwise about fold line 51 until second side support panel 70 is perpendicular to the top panel 50. Than, first top support panel 80 is rotated clockwise about fold line 71 until first top support panel 80 is perpendicular to second side panel 70. Next, first side support panel 90 is rotated clockwise about fold line 81 such that first side support 90 is perpendicular to first top support panel 80 and top panel 50 and the connecting panel 100 is rotated counter-clockwise about fold line 91 such that the connecting panel 100 is perpendicular to first side support panel 90 and parallel to the top panel 50, resting upon the top panel 50, and having a configuration as shown in FIG. 5. Although not required, it is preferred to mount the inner side of the connecting panel 100 to the inner side of the top panel 50 using an adhesive, cement, or other bonding agents and equivalents thereof. If desired, it is also possible to mechanically attach the connecting panel 100 to the top panel 50 using staples, rivets, and other types of mechanical fasteners. It is also possible to use tabs and tab pockets.

Referring to FIG. 5, the major side support members 170 and 180 can be seen. Support member 170 consists of the second side panel 70, the first top support panel 80 and the first side support panel 90. The second major side support member 180 consists of the second side support panel 110 and the second top support panel 20. An end view showing the support members 170 an 180 is seen in FIG. 5A.

Referring next to FIGS. 1, 3, 6, and 7, the next step in the assembly is seen to be the rotation of the top panel 50, the connecting panel 100, and the side members 170 and 180 clockwise about fold line 41 such that the first side panel 40 is substantially perpendicular to the base panel 50. Then, top panel 50, connecting panel 100, the side member 170 and 180 and the first side panel 40 are rotated clockwise about the fold line 22 such that first side panel 40 is substantially perpendicular to the base panel 20. Next, the closure flap 30 is rotated counter-clockwise about the fold line 21 such that the closure flap is substantially perpendicular to second side panel 70. The closure flap 30 is preferably mounted to second side panel 70 using adhesives, glues, mechanical fasteners, tabs, and tab pockets, and the like.

Next, the first end support member 190 and the second end support member 200 are assembled. Initially, second end support member 200 is assembled by initially folding top flap panel 160 about fold line 151 such that top flap panel 160 is substantially perpendicular to inner flap panel 150. Next, inner flap panel 150 is folded about fold line 141 such that inner flap 150 is substantially perpendicular to bottom flap panel 140. Next, outer flap panel 130 is folded about fold line 21 such that outer flap panel 130 is substantially perpendicular to base panel 20 and top panel 50 thereby forming second end support member 200. The first end support 190 is assembled in a similar matter. The first and second end support members 190 and 200 are locked by inserting the tabs 60 in the pockets 136.

Figure 1:
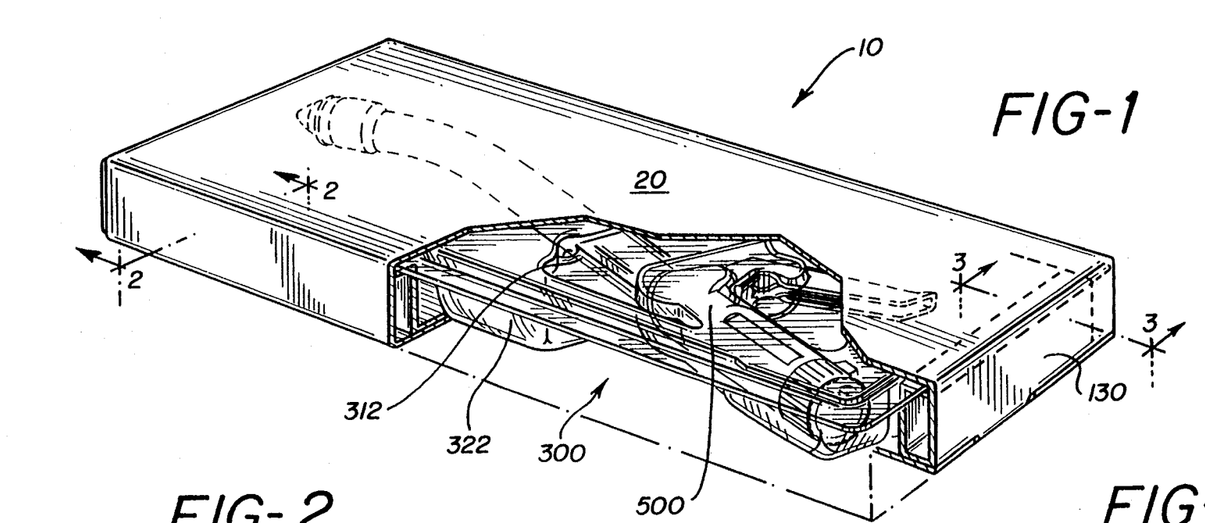
FIG. 1 is a perspective view of a package of the present invention containing a sealed, thermoformed blister package which contains a sterile instrument. A partial cutaway section illustrates the inner blister package and instrument.
Figure 2:
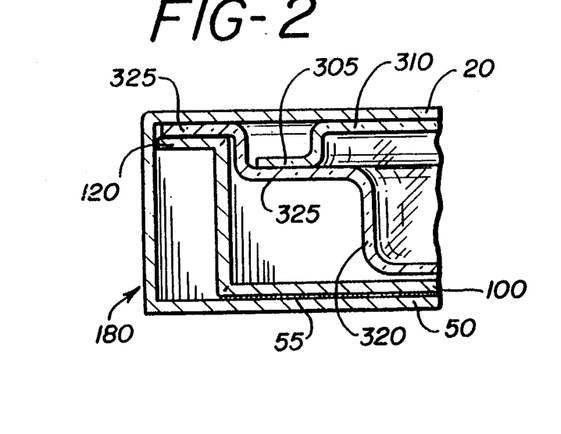
FIG. 2 is a partial cutaway view of the package of FIG. 1 taken along View Line 2—2 illustrating support of a flange of the thermoformed blister package.

It can be seen referring to FIGS. 1, 2, and 3 that the first and second side support members 170 and 180 and the first and second end support members 190 and 200 substantially support the outwardly extending flange 325 and seal 305 of the blister package 300. In addition, the integral support members stiffen the package thereby reducing flexing. Although not preferred, the end support members 190 and 200 may be replaced by conventional end flaps, however the end sections of the flanges 325 would not be supported.

The packages 10 have many advantages. The package 10 is relatively inexpensive and easy to manufacture from recyclable materials. The use of the package 10 provides support for the flange 125 of a blister packaged instrument 100 and provides a package which resists flexion or torsion during handling, shipping, storage and sterilization, thereby helping to protect the seal 325 from damage. The use of the package 10 can eliminate the need for foam cushioning and oversize outer packages. Yet another advantage is that the supporting members 170, 180, 190, and 200 are integral with the package 10 (i.e., package 10 is one piece) and no separate supporting member needs to be inserted.

Although this invention has been shown and described with respect to detailed embodiments thereof, it will be understood by those skilled in the art that various changes in form and detail thereof may be made without departing from the spirit and scope of the claimed invention.

What is claimed is:

1. In combination:
   a foldable outer package comprising a base panel having a pair of opposed major sides and a pair of opposed minor sides;
   a first side panel having a pair of opposed major sides and a pair of opposed minor sides, wherein the first side panel is foldably connected along a first major side to a first major side of the base panel;
   a closure flap foldably connected to a second major side of the base panel;
   a top panel having a pair of opposed major sides and a pair of opposed minor sides, wherein the top panel is foldably connected along a first major side to the second major side of the first side panel;
   a second side panel having a pair of opposed major sides and a pair of opposed minor sides, the second side panel foldably connected along a first major side to a second major side of the first side panel;
   a first top support panel having a pair of opposed major sides and a pair of opposed minor sides wherein the first top support panel is foldably connected along a first major side to a second major side of the second side panel;
   a first side support panel having a pair of opposed major sides and a pair of opposed minor sides foldably connected along a first major side to a second major side of the first top support panel;
   a connecting panel having a pair of opposed major sides and a pair of opposed minor sides, the connecting panel foldably connected along a first major side to a second major side of the first side support panel;
   a second side support panel having a pair of opposed major sides and a pair of opposed minor sides, the second side support panel foldably connected along a first major side to a second major side of the connecting panel;
   a second top support panel having a pair of opposed major sides and a pair of opposed minor sides, the second top support panel foldably connected along a major side to a second major side of the second side support panel;
   a end closure means foldably connected to each minor side of the base panel; and
   a package placed within said foldable outer package through the opening formed by said connecting panel, said first side support panel, said top panel and said second side support panel when one of said end closure means is open, said package containing a surgical instrument.

2. The foldable outer package of claim 1 wherein the end closure means comprises:
   an outer flap panel having a pair of opposed minor sides and a pair of opposed major sides wherein the outer panel is foldably connected along a first major side to a minor side of the base panel;
   a bottom flap panel having a pair of opposed major sides and a pair of opposed minor sides, the bottom flap panel foldably connected along a first major side to a second major side of the outer flap panel;
   an inner flap panel having a pair of opposed major sides and a pair of opposed minor sides foldably connected along a first major side to a second major side of the bottom flap panel; and,
   a top flap panel having a pair of opposed major sides and a pair of opposed minor sides foldably connected along a major side to a second major side of the inner flap panel.

3. The foldable package of claim 2 additionally comprising means for locking the end closure means.

4. The package of claim 3 wherein the locking means comprises a tab means extending from each minor side of the top panel and tab pocket means for receiving the tab means in the end closure means.

5. The package of claim 2 further comprising a tray having an outwardly extending flange.

6. In combination:
   a foldable outer package comprising a base panel having a pair of opposed major sides and a pair of opposed minor sides;
   a first side panel having a pair of opposed major sides and a pair of opposed minor sides, wherein the first side panel is foldably connected along a first major side to a first major side of the base panel;
   a closure flap foldably connected to a second major side of the base panel;
   a top panel having a pair of opposed major sides and a pair of opposed minor sides, wherein the top panel is foldably connected along a first major side to the second major side of the first side panel;
   a second side panel having a pair of opposed major sides and a pair of opposed minor sides, the second side panel foldably connected along a first major side to a second major side of the first side panel;
   a first top support panel having a pair of opposed major sides and a pair of opposed minor sides wherein the first top support panel is foldably connected along a first major side to a second major side of the second side panel;
   a first side support panel having a pair of opposed major sides and a pair of opposed minor sides foldably connected along a first major side to a second major side of the first top support panel;
   a connecting panel having a pair of opposed major sides and a pair of opposed minor sides, the connecting panel foldably connected along a first major side to a second major side of the first side support panel;
   a second side support panel having a pair of opposed major sides and a pair of opposed minor sides, the second side support panel foldably connected along a first major side to a second major side of the connecting panel;
   a second top support panel having a pair of opposed major sides and a pair of opposed minor sides, the second top support panel foldably connected along a major side to a second major side of the second side support panel;

a end closure means foldably connected to each minor side of the base panel; and a package placed within said foldable outer package through the opening formed by said connecting panel, said first side support panel, said top panel and said second side support panel when one of said end closure means is open, said package containing a surgical instrument;

further comprising a thermoformed tray having an outwardly extending flange; and said flange engaging at least one of said top support panels and said top panel.

* * * * *